United States Patent [19]

Kagitani et al.

[11] 4,265,888

[45] May 5, 1981

[54] ACETYLSALICYLATE POWDER PREPARATION FOR INJECTION

[75] Inventors: Yoshio Kagitani, Kashiwara; Takashi Imagawa, Sakai; Hirohisa Inahara, Kyoto; Ryozo Watanabe, Takatsuki, all of Japan

[73] Assignee: The Green Cross Corporation, Osaka, Japan

[21] Appl. No.: 110,753

[22] Filed: Jan. 8, 1980

[30] Foreign Application Priority Data

Jul. 6, 1979 [JP] Japan ................................ 54-85596

[51] Int. Cl.³ .......................................... A61K 31/615
[52] U.S. Cl. .................................................... 424/233
[58] Field of Search ......................................... 424/233

[56] References Cited

U.S. PATENT DOCUMENTS

| 2,101,867 | 12/1937 | Miller et al. | 424/233 |
| 3,392,195 | 7/1968 | Galat | 424/233 |

Primary Examiner—Stanley J. Friedman
Attorney, Agent, or Firm—Cushman, Darby & Cushman

[57] ABSTRACT

Acetylsalicylates with basic amino acids such as DL-lysine is stabilized in the form of solid preparation by admixing anhydrous calcium chloride therewith. The preparation containing calcium chloride is prevented from hydrolysis and can be stored for a long period of time even at a relatively high room temperature. The preparation is further prevented from discarolation when glycine is added thereto.

2 Claims, No Drawings

ACETYLSALICYLATE POWDER PREPARATION FOR INJECTION

This invention relates to an acetylsalicylate powder preparation for injection and, more particularly, to an acetylsalicylate powder preparation for injection characterized by containing calcium chloride as stabilizer.

Acetylsalicylic acid (aspirin) has long been used as an analgesic, antipyretic and antirheumatic, more recently, it is widely used as a non-steroid anti-inflammatory in treating arthritis, neuralgia and myalgia.

Because of its limited solubility in water (about 0.3%), aspirin has heretofore been prescribed as an oral drug. When orally administered, however, it is hydrolyzed by the strongly acidic gastric juice, forming salicylic acid which irritates the gastric mucosa. To avoid this, an enteric coated tablet or other modified preparations have been devised. In spite of such modification, orally administered acetylsalicylic acid is not completely absorbed and is unavoidably slow in the onset of pharmaceutical action. On the other hand, the effectiveness of intravenously administered acetylsalicylic acid is said to be four times as high as that of the orally administered equal amount of acetylsalicylic acid.

In order to improve the method for adminstrating acetylsalicylic acid, the present inventors had attempted to prepare a derivative suitable for injection and succeeded in preparing a salt easily soluble in water (40% or more insolubility) by reacting acetylsalicylic acid and a basic amino acid in the molar ratio of 1:1 (Japanese Patent Application Laid-open No. 56,815/1973). Because of its instability in an aqueous medium, the acetylsalicylate of basic amino acid (hereinafter referred to simply as the acetylsalicylate) must be in the form of powder in order to insure stability until the time when it is used as an injection. According to Japanese Patent Application cited above, the powder is prepared by lyophilization or by crystallization from aqueous alcohol by the addition of a precipitant.

The acetylsalicylate is also unstable to heat and, for this reason, there were present a number of problems in its commercial production. If exposed to heat in a customary manner in the sterilization and drying treatments required for its use as an injection, a greater part of acetylsalicylate undergoes decomposition. The present inventors previously studied the reaction conditions to overcome the difficulties and succeeded in establishing a method for producing the acetylsalicylate in good yields by properly selecting the reaction solvent and the precipitant (Japanese Patent Application Laid-open No. 44,623/1976).

Although, as described above, a process suitable for the commercial production of the acetylsalicylate for injection was established, the powdered salt produced was still unsatisfactory in storage stability and, though stable during the storage at 4° C., acetylsalicylate becomes unstable with the increase in temperature, forming salicylic acid even at room temperature on long storage. The acetylsalicylate for injection was developed for the purpose of rapid onset of action in the living body by, for example, intravenous administration. Therefore, it is important that the preparation is reserved in a hospital in the state being able to place it at a service whenever needed. This requires the preparation comprising the acetylsalicylate to be stable enough for long storage. If, in spite of the requirement, the supplied preparation tends to form impurities with time, the preparation might cause side effects on being administered, and the commercial value of the preparation will be markedly decreased or even become valueless as a defective article of commerce.

Consequently, the present inventors carried out extensive investigations to find a measure to be taken for the improvement in storage stability of the powder preparation containing the acetylsalicylate. As a result, it was found that a more stable preparation can be obtained by the addition of a stabilizer, and the finding has led to the accomplishment of this invention.

According to this invention, there is provided a pharmaceutical composition comprising an injection powder preparation of an acetylsalicylate obtained by reacting a acetylsalicylic acid and a basic amino acid and incorporated with 1% (W/W) or more based on the powder preparation of calcium chloride.

The acetylsalicylate used in this invention can be prepared by the methods disclosed in Japanese Patent Application Laid-open No. 44,623/1976 and No. 56,815/1973. The preferred basic amino acid is DL-lysine. In DL-lysine acetylsalicylate, both reactants are combined in the molar ratio of 1:1, conforming to the structural formula:

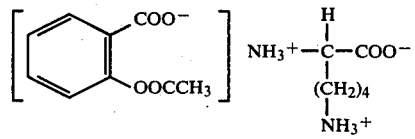

Chemical name: DL-lysine acetylsalicylate
Molecular formula: $C_{15}H_{22}O_6N_2$
Molecular weight: 326.35

The salt is a white crystalline powder and odorless. An example of preparative procedure is given below.

EXAMPLE OF PREPARATIVE PROCEDURE

I. Reaction step

In 100 liters of pyrogen-free distilled water, are dissolved 5.8 kg of glycine and 23.25 kg of DL-lysine. The solution is treated with about 600 g of activated carbon to remove coloring matters originated mainly from DL-lysine. The filtrate is mixed with a suspension of 30 kg of acetylsalicylic acid in 60 liters of aceton. After the acetylsalicylic acid has been dissolved, forming a clear solution, the reaction mixture is sterilized by bacterial filtration and sent to a crystallization tank.

II. Crystallization step

To the sterile reaction mixture, is added 150 liters of acetone which has been sterilized by bacterial filtration. After mild stirring, the resulting solution is left standing in a cooling chamber at 0° to 6° C. for about 20 hours to form the crystalline seeds. After addition of 150 liters of sterile acetone, the solution was left standing in a cooling chamber for 24 hours to allow the crystals to grow. The crystals are aseptically collected by filtration.

III. Washing and drying step

The collected crystals are washed by adding 100 liters of a 90% aqueous acetone solution sterilized by bacterial filtration. After further washing with 200 liters of acetone, the crystals are dried under an air current to a moisture content of 1.0% or less to obtain about 35 kg of sterile crystals.

The calcium chloride for use as the stabilizer is preferably an anhydrous one, though any of other pharmaceutically acceptable grades may be used. The amount of stabilizer to be added is 1% (W/W) or more, preferably 3 to 6% (W/W) based on the finally stabilized acetylsalicylate powder. If necessary, 1 to 10% (W/W) of an anti-discoloration agent such as glycine may be freely added. In preparing the final preparation, at first a predetermined amount of calcium chloride is added to a cleansed dispensing container, then heated at 150° to 180° C. for 4 hours and allowed to cool in a desiccator containing phosphorus pentoxide or in a drying box. When the calcium chloride has been cooled below room temperature, 1 g of the acetylsalicylate is added to the container containing the calcium chloride and the container is sealed off. Alternatively, a quantity of calcium chloride is heated at 150° to 180° C. for 4 hours, then allowed to cool in a desiccator containing phosphorus pentoxide or in a drying box, and is then pulverized in a sterile ball mill. The powdered material is aseptically mixed thoroughly with 99 times or less, preferably 30 to 20 times its weight of the acetylsalicylate and placed portionwise in ampules or vials which are then sealed by heat or sealed with gum stopper and then crimped with an aluminum cap.

Experiment on the effect of addition of calcium chloride:

Samples for testing the effect of addition of calcium chloride were prepared in the following manner.

Amount added of calcium chloride: Six groups of samples were prepared by adding 50, 40, 20, 10, 5 and 0 mg of calcium chloride to each 1 g of the DL-lysine acetylsalicylate prepared in the aforementioned example of preparative procedure.

Storage temperature: Each group of samples was stored at three different temperatures of 25°, 32° and 45° C.

A group of samples stored at 4° C. was used as control. Tests were performed after 0, 1, 2, 4 and 10 weeks of storage. The test item was the amount of salicylic acid formed which was quantitatively determined by high-speed liquid chromatography. The results obtained were shown in Table 1.

Table 1 shows the change in the formation of salicylic acid with the duration of storage. It is seen from Table 1 that the formation of salicylic acid is decreased with the increase in the amount of calcium chloride added. When calcium chloride is added in an amount of 5 mg/g, the formation of salicylic acid at 32° C. is controlled for 4 weeks of storage, but becomes very marked after 10 weeks of storage. By the addition of 10 mg/g, a certain degree of effectiveness of calcium chloride can be exhibited. Increased inhibition of the formation of salicylic acid is observed by the addition of 20 or 40 mg/g of calcium chloride. It is seen from the results that formation of salicylic acid is more inhibited with the increase in the amount of calcium chloride. When calcium chloride is added in an amount of 40 mg/g or more, the increased formation of salicylic acid with time at 25° C. is completely inhibited.

TABLE 1

Change in the formation of salicylic acid with the amount of calcium chloride.

| Sample (CaCl₂ mg/g) | Temp. of storage (°C.) | Salicylic acid content (%) after | | | | |
|---|---|---|---|---|---|---|
| | | 0 week | 1 week | 2 weeks | 4 weeks | 10 weeks |
| 50 | | | 1.25 | 3.28 | 9.01 | |
| 40 | | | 1.28 | 3.32 | 9.04 | |
| 20 | | | 1.53 | 3.90 | 16.46 | |
| | 45 | 0.42 | | | | |
| 10 | | | 1.80 | 5.57 | 19.58 | |
| 5 | | | 4.83 | 17.61 | 29.22 | |
| 0 | | | 13.29 | 27.58 | — | |
| 50 | | | 0.49 | 0.81 | 1.05 | 1.68 |
| 40 | | | 0.55 | 0.85 | 1.09 | 1.76 |
| 20 | | | 0.64 | 0.86 | 1.14 | 2.39 |
| | 32 | 0.42 | | | | |
| 10 | | | 0.52 | 0.87 | 0.98 | 2.96 |
| 5 | | | 0.52 | 0.96 | 1.29 | 10.09 |
| 0 | | | 1.49 | 3.17 | 6.15 | 16.40 |
| 50 | | | 0.44 | 0.45 | 0.49 | 0.59 |
| 40 | | | 0.45 | 0.45 | 0.47 | 0.62 |
| 20 | | | 0.48 | 0.49 | 0.59 | 0.94 |
| | 25 | 0.42 | | | | |
| 10 | | | 0.48 | 0.51 | 0.66 | 1.02 |
| 5 | | | 0.49 | 0.53 | 0.81 | 1.17 |
| 0 | | | 0.73 | 1.21 | 1.48 | 3.05 |
| 0 | 4 | 0.42 | 0.51 | 0.76 | 0.97 | 1.653 |

In using the preparation of this invention, it is dissolved in distilled water for injection (5 to 20 ml of water for 1 g of the preparation) and administered intravenously. The adult dose is usually 1 to 2 vials (1 vial contains 1,050 mg). For repetitive administration, a recommendable daily dose is up to 5 vials. The daily dose in terms of salicylic acid for infants and children is 10 to 25 mg per kilogram of body weight, which is administered in 2 or 3 divided doses.

The diseases for which the preparation of this invention is efficacious include post-operational pain and other pains for which oral administration of an analgesic is effective; rheumatoid diseases (especially efficacious for progressive rheumatoid), neuralgia and neuritis; and hyperthermia (common cold, bronchitis and other central fever).

Acute toxicity test:

The test animals used were dd-strain mice (each 20±1 g in body weight and 4 to 5 weeks old). A preparation of the composition shown later was dissolved in distilled water to prepare solutions of varied concentrations. Each solution was administered intravenously, subcutaneously or orally to each group of 10 female or 10 male mice. The symptoms of poisoning and the condition of death were observed for a period of seven days. All animals died in the observed period and those survived beyond said period were autopsied to observe visually the anomalies if any. $LD_{50}$ values for the mice were as summarized in Table 2.

TABLE 2

| Route of administration | Sex | $LD_{50}$ (95% confidence limits) |
|---|---|---|
| Intravenous | Male | 1070 (870–1320) |
| | Female | 950 (740–1220) |
| Subcutaneous | Male | 1840 (1670–2020) |
| | Female | 2100 (1850–2380) |
| Oral | Male | 3500 (2650–4620) |
| | Female | 3270 (2420–4420) |

Preparation used for toxicity test:

| | |
|---|---|
| DL-lysine acetylsalicylate | 900 mg |
| Aminoacetic acid (JP), anti-discoloration agent | 100 mg |
| Calcium chloride (anhydrous), stabilizer | 50 mg |
| Total | 1,050 mg |

The active ingredient DL-lysine acetylsalicylate (900 mg) is a salt composed by acetylsalicylic acid (498 mg) and DL-lysine (402 mg).

What is claimed is:

1. A pharmaceutical composition comprising an effective amount of acetylsalicylate of DL-lysine characterized in that the pharmaceutical composition is a solid and contains 3–6% by weight of anhydrous calcium chloride based on the total weight of the acetylsalicylate and the anhydrous calcium chloride.

2. The pharmaceutical composition of claim 1, wherein it contains additionally glycine in an amount sufficient for preventing discoloration of the composition.

* * * * *